(12) United States Patent
Akutsu et al.

(10) Patent No.: US 7,696,257 B2
(45) Date of Patent: Apr. 13, 2010

(54) OXIME ESTER COMPOUND AND PHOTOPOLYMERIZATION INITIATOR CONTAINING SUCH COMPOUND

(75) Inventors: Mitsuo Akutsu, Tokyo (JP); Daisuke Sawamoto, Tokyo (JP); Yasunori Kozaki, Tokyo (JP); Toshihiko Murai, Tokyo (JP)

(73) Assignee: Adeka Corporation, Tokyo (JP)

( * ) Notice: Subject to any disclaimer, the term of this patent is extended or adjusted under 35 U.S.C. 154(b) by 526 days.

(21) Appl. No.: 11/659,979

(22) PCT Filed: Aug. 3, 2005

(86) PCT No.: PCT/JP2005/014190
§ 371 (c)(1), (2), (4) Date: Feb. 12, 2007

(87) PCT Pub. No.: WO2006/018973
PCT Pub. Date: Feb. 23, 2006

(65) Prior Publication Data
US 2007/0270522 A1 Nov. 22, 2007

(30) Foreign Application Priority Data

| Aug. 20, 2004 | (JP) | 2004-241370 |
| May 20, 2005 | (JP) | 2005-148007 |
| Jul. 11, 2005 | (JP) | 2005-201128 |

(51) Int. Cl.
C08F 2/50 (2006.01)
C07C 251/00 (2006.01)
C07D 405/12 (2006.01)
C07D 409/12 (2006.01)
C07D 421/12 (2006.01)

(52) U.S. Cl. ........... 522/16; 522/18; 522/26; 522/28; 522/39; 522/65; 548/440; 548/444; 564/253; 564/254

(58) Field of Classification Search .......... 522/63, 522/65, 68, 16, 18, 26, 28, 39; 564/248, 564/253, 254; 548/440, 444
See application file for complete search history.

(56) References Cited

U.S. PATENT DOCUMENTS

| 3,558,309 | A | 1/1971 | Laridon et al. |
| 4,202,697 | A | 5/1980 | Van Goethem et al. |
| 4,255,513 | A | 3/1981 | Laridon et al. |
| 4,590,145 | A | 5/1986 | Itoh et al. |
| 6,949,678 | B2 * | 9/2005 | Kunimoto et al. ........... 564/255 |
| 7,189,489 | B2 * | 3/2007 | Kunimoto et al. ........ 430/270.1 |

FOREIGN PATENT DOCUMENTS

| DE | 100 61 947 | | 6/2001 |
| JP | 2000-080068 | | 3/2000 |
| JP | 2001-233842 | | 8/2001 |
| JP | 2001233842 A | * | 8/2001 |
| JP | 2006-036750 | * | 2/2005 |
| JP | 2005/202252 | | 7/2005 |
| WO | 02/100903 | | 6/2002 |
| WO | 2004/050653 | | 6/2004 |
| WO | WO 2004050653 A2 | * | 6/2004 |
| WO | WO 2005080337 | * | 2/2005 |
| WO | WO 2006018405 A1 | * | 2/2006 |

OTHER PUBLICATIONS

European Patent Office issued an European Search Report dated Apr. 28, 2009, Application No. 05 76 8407.

* cited by examiner

*Primary Examiner*—Susan W Berman
(74) *Attorney, Agent, or Firm*—Young & Thompson

(57) ABSTRACT

An oxime ester compound represented below is useful as a photopolymerization initiator. A photopolymerization initiator including this as an active constituent has high sensitivity and causes no concern about coloration or contamination.

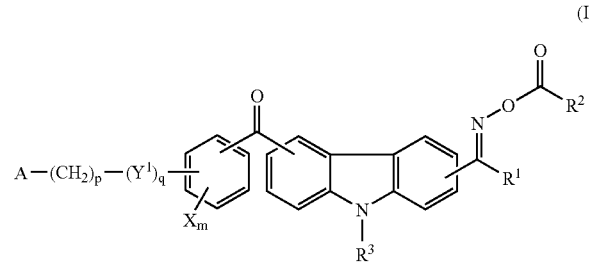

(X represents a halogen atom or alkyl group. $R^1$, $R^2$, and $R^3$ each independently represent R, OR, COR, SR, CONRR', or CN, wherein R and R' each represent an alkyl group, an aryl group, an aralkyl group, or a heterocyclic group; these groups may be substituted with (a) halogen atom(s) and/or (a) heterocyclic group(s); the alkylene moiety in the alkyl or aralkyl group may be interrupted by (an) unsaturated bond(s), (an) ether bond(s), (a) thioether bond(s), or (an) ester bond(s); and R and R' may form a ring. $Y^1$ represents an oxygen, sulfur, or selenium atom; A represents a heterocyclic group; m represents an integer 0-4; p represents an integer 0-5; and q represents 0 or 1.)

16 Claims, No Drawings

OXIME ESTER COMPOUND AND PHOTOPOLYMERIZATION INITIATOR CONTAINING SUCH COMPOUND

TECHNICAL FIELD

The present invention relates to a novel oxime ester compound useful as a photopolymerization initiator used in a photosensitive composition, a photopolymerization initiator containing the oxime ester compound as an active constituent, and a photosensitive composition comprising adding the photopolymerization initiator to a polymerizable compound having (an) ethylenic unsaturated bond(s).

BACKGROUND ARTS

A photosensitive composition is a composition in which a photopolymerization initiator is added to a polymerizable compound having (an) ethylenic unsaturated bond(s). Since the photosensitive composition can be cured through polymerization on irradiation with 405-nm or 365-nm light, it is used for photocurable inks, photosensitive plates, various types of photoresists, and the like. Since a photosensitive composition sensitive to a shorter wavelength light source facilitates printing at higher resolution, there has been demand for a photopolymerization initiator with particularly high sensitivity to a 365-nm light source.

Patent Document 1 below proposed the use of an oxime ester derivative as a photopolymerization initiator used in such a photosensitive composition, and Patent Documents 2 to 4 below also described oxime ester compounds. When any of these publicly known oxime ester compounds was used as a photopolymerization initiator, however, decomposition products which generated on exposure attached to a mask, causing fault in the pattern shape on printing, and hence lowering the yield. In addition, since these oxime ester compounds have a decomposition temperature of 240° C. or lower, the photopolymerization initiator may decompose in a post-development thermosetting treatment which is typically performed at 130 to 240° C., possibly deteriorating properties of the resultant resin. For this reason, the thermosetting treatment was required to be performed at lower temperature for a long duration. Although thermosetting treatment at higher temperatures could shorten the duration of treatment, the properties of resins would be deteriorated by heat. Thus, in thermosetting treatment at higher temperatures, a photopolymerization initiator with higher heat resistance is required. It has been, therefore, desired a photopolymerization initiator with a decomposition temperature of 240° C. or higher that causes neither coloration of the resultant polymerized material nor generation of decomposition products that may diffuse as vapor and contaminate the polymerized material, apparatuses, or the like.

Patent Documents 5 to 8 below proposed O-acyloxime photopolymerization initiators with higher reactivity. These O-acyloxime photopolymerization initiators, however, were still unsatisfactory in terms of sensitivity, and a more sensitive photopolymerization initiator has been desired. Patent Document 7 below disclosed an O-acyloxime compound having a carbazolyl moiety, but that compound was not satisfactory in terms of sensitivity, resolution, or alkali resistance either.

Patent Document 1: U.S. Pat. No. 3,558,309
Patent Document 2: U.S. Pat. No. 4,255,513
Patent Document 3: U.S. Pat. No. 4,590,145
Patent Document 4: U.S. Pat. No. 4,202,697
Patent Document 5: JP-A-2000-80068
Patent Document 6: JP-A-2001-233842
Patent Document 7: WO 02/100903
Patent Document 8: WO 2004/050653

DISCLOSURE OF THE INVENTION

Problems to be Solved by Invention

As described above, the problem to be resolved is that there has been no photopolymerization initiator that has high sensitivity and causes neither coloration of the resultant polymerized material nor contamination of the polymerized material, apparatuses, or the like.

An object of the present invention is, therefore, to provide a photopolymerization initiator that has high sensitivity and causes neither coloration of the resultant polymerized material nor contamination of the polymerized material, apparatuses, or the like.

Means for Solving the Problems

The present invention provides an oxime ester compound represented by general formula (I) below and a photopolymerization initiator comprising the compound as an active constituent, thereby achieving the above object.

[Chemical Formula 1]

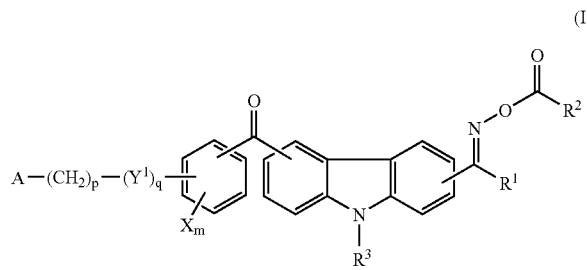

(I)

(In the formula, X represents a halogen atom or an alkyl group. $R^1$, $R^2$, and $R^3$ each independently represent R, OR, COR, SR, CONRR', or CN, wherein R and R' each represent an alkyl group, an aryl group, an aralkyl group, or a heterocyclic group; these groups may be substituted with (a) halogen atom(s) and/or (a) heterocyclic group(s); the alkylene moiety in the alkyl or aralkyl group may be interrupted by (an) unsaturated bond(s), (an) ether bond(s), (a) thioether bond(s), or (an) ester bond(s); and R and R' may bond together to form a ring. $Y^1$ represents an oxygen atom, a sulfur atom, or a selenium atom; A represents a heterocyclic group; m represents an integer of 0 to 4; p represents an integer of 0 to 5; and q represents 0 or 1.)

The present invention also provides a photosensitive composition comprising adding the above photopolymerization initiator to a photopolymerizable compound having (an) ethylenic unsaturated bond(s), and a colored photosensitive composition comprising adding an additional colorant to the photosensitive composition.

BEST MODE FOR CARRYING OUT THE INVENTION

Detail description will be given below about the oxime ester compound of the present invention and the photopolymerization initiator of the present invention comprising the compound as an active constituent.

In general formula (I), the alkyl group represented by R or R' includes, for example, methyl, ethyl, propyl, isopropyl, butyl, isobutyl, sec-butyl, tert-butyl, amyl, isoamyl, tert-amyl, hexyl, heptyl, octyl, isooctyl, 2-ethylhexyl, tert-octyl, nonyl, isononyl, decyl, isodecyl, vinyl, allyl, butenyl, ethynyl, propynyl, methoxyethyl, ethoxyethyl, propyloxyethyl, methoxyethoxyethyl, ethoxyethoxyethyl, propyloxyethoxyethyl, methoxypropyl, monofluoromethyl, difluoromethyl, trifluoromethyl, trifluoroethyl, perfluoroethyl, 2-(benzoxazol-2'-yl)

ethenyl, and the like. Among these, alkyl groups having 1 to 8 carbon atoms are preferred. The aryl group represented by R or R' includes, for example, phenyl, tolyl, xylyl, ethylphenyl, chlorophenyl, naphthyl, anthryl, phenanthryl, and the like. Among these, aryl groups having 6 to 12 carbon atoms are preferred. Preferred examples of the aralkyl group represented by R or R' include aralkyl groups having 7 to 13 carbon atoms such as benzyl, chlorobenzyl, α-methylbenzyl, α,α-dimethylbenzyl, phenylethyl, and phenylethenyl. Preferred examples of the heterocyclic group represented by R or R' include 5- to 7-membered heterocyclic groups such as pyridyl, pyrimidyl, furyl, and thiophenyl. As the ring that can be formed when R and R' bond together, 5- to 7-membered rings such as piperidine ring and morpholine ring are preferred.

The halogen atom that may be contained in R and R' as a substituent includes chlorine, bromine, and iodine as well as fluorine, which is evidently seen also in the above list of the alkyl group. The heterocyclic group that may be contained in R and R' as a substituent includes, for example, 5- to 7-membered heterocyclic groups such as pyridyl, pyrimidyl, furyl, benzoxazol-2-yl, tetrahydropyranyl, pyrrolidyl, imidazolidyl, pyrazolidyl, thiazolidyl, isothiazolidyl, oxazolidyl, isooxazolidyl, piperidyl, piperazyl, and morpholinyl.

The halogen atom represented by X includes fluorine, chlorine, bromine, and iodine. As is the case of R and R', the alkyl group represented by X may be substituted with (a) halogen atom(s) and/or (a) heterocyclic group(s), wherein the alkylene moiety in the alkyl group may be interrupted by (an) unsaturated bond(s), (an) ether bond(s), (a) thioether bond(s), or (an) ester bond(s). The alkyl group represented by X includes, for example, methyl, ethyl, propyl, isopropyl, butyl, isobutyl, sec-butyl, tert-butyl, amyl, isoamyl, tert-amyl, hexyl, heptyl, octyl, isooctyl, 2-ethylhexyl, tert-octyl, nonyl, isononyl, decyl, isodecyl, vinyl, allyl, butenyl, ethynyl, propynyl, methoxyethyl, ethoxyethyl, propyloxyethyl, methoxyethoxyethyl, ethoxyethoxyethyl, propyloxyethoxyethyl, methoxypropyl, monofluoromethyl, difluoromethyl, trifluoromethyl, trifluoroethyl, perfluoroethyl, 2-(benzoxazol-2'-yl)ethenyl, and the like. Among these, alkyl groups having 1 to 8 carbon atoms are preferred.

The heterocyclic group represented by A includes, for example, 1,3-dioxolanyl, 2-tetrahydrofuryl, 3-tetrahydrofuryl, 2-tetrahydrothienyl, 2-oxiryl, 2-aziridinyl, 2-furyl, 3-furyl, 2-thienyl, 2-pyridyl, 2-pyranyl, 2-thiazoyl, 2-imidazolyl, 2-pyrazolyl, 2-oxazolyl, 2-pyrazinyl, 2-pyrimidinyl, 2-quinolyl, 2-carbazolyl, and the like. These heterocyclic groups may be substituted with (a) halogen atom(s) or (an) alkyl group(s), and such a halogenated or alkylated heterocyclic group includes, for example, 2,2-dimethyl-1,3-dioxolanyl and 2-chloro-2-methyl-1,3-dioxolanyl. In particular, the heterocyclic group represented by A is preferably 1,3-dioxolanyl, 2-tetrahydrofuryl, or 2-furyl, wherein said group is optionally substituted with (a) halogen atom(s) or (an) alkyl group(s). Especially preferred groups are 2,2-dimethyl-1,3-dioxolanyl, unsubstituted 2-tetrahydrofuryl, and unsubstituted 2-furyl because of their advantages in production cost and the absorption wavelength.

Preferred examples of the oxime ester compound of the present invention include compounds represented by any of general formulae (II) to (IV) below. The heterocyclic group represented by A in general formula (I) is 1,3-dioxolanyl optionally substituted with (a) halogen atom(s) or (an) alkyl group(s) in general formula (II), 2-tetrahydrofuryl optionally substituted with (a) halogen atom(s) or (an) alkyl group(s) in general formula (III), or 2-furyl optionally substituted with (a) halogen atom(s) or (an) alkyl group(s) in general formula (IV).

[Chemical Formula 2]

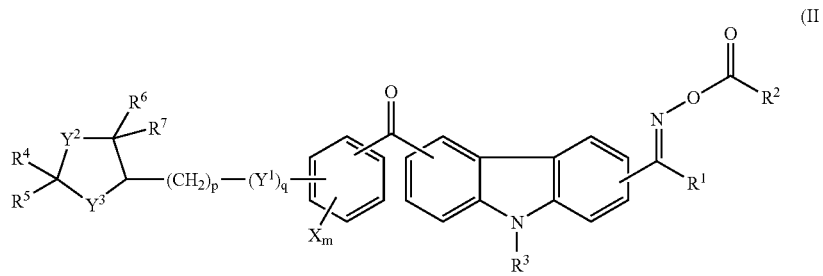

(II)

(In the formula, $R^1$, $R^2$, $R^3$, X, $Y^1$, m, p, and q are as defined in general formula (I); $R^4$, $R^5$, $R^6$, and $R^7$ each independently represent a hydrogen atom, a halogen atom, or an alkyl group; and $Y^2$ and $Y^3$ each independently represent an oxygen atom, a sulfur atom, or a selenium atom.)

[Chemical Formula 3]

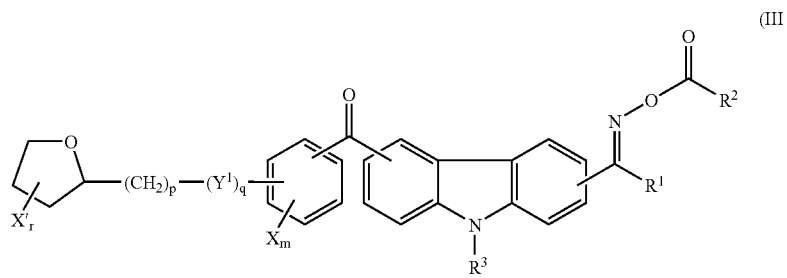

(III)

(In the formula, $R^1$, $R^2$, $R^3$, X, $Y^1$, m, p, and q are as defined in general formula (I); X' represents a halogen atom or an alkyl group; and r represents an integer of 0 to 4.)

[Chemical Formula 4]

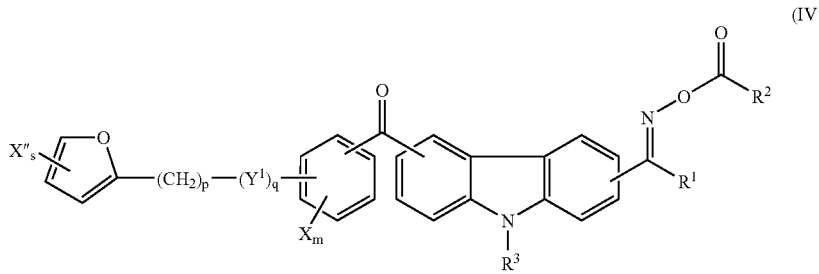

(IV)

(In the formula, $R^1$, $R^2$, $R^3$, X, $Y^1$, m, p, and q are as defined in general formula (I); X" represents a halogen atom or an alkyl group; and s represents an integer of 0 to 3.)

In general formulae (II) to (IV), the halogen atom represented by $R^4$, $R^5$, $R^6$, $R^7$, X', or X" includes fluorine, chlorine, bromine, and iodine. As is the case of R and R', the alkyl group represented by $R^4$, $R^5$, $R^6$, $R^7$, X', or X" In general formulae (II) to (IV) may be substituted with (a) halogen atom(s) and/or (a) heterocyclic group(s), and the alkylene moiety in the alkyl group may be interrupted by (an) unsaturated bond(s), (an) ether bond(s), (a) thioether bond(s), or (an) ester bond(s). The specific examples and preferred examples are the same as those listed for R and R'.

In general formulae (I) to (IV), $R^1$ is preferably an alkyl group, particularly methyl; $R^2$ is preferably an alkyl group, particularly methyl; $R^3$ is preferably an alkyl group, particularly ethyl; X is preferably an alkyl group, particularly methyl; $Y^1$ is preferably an oxygen atom; p is preferably 1 or 2; q is preferably 1; and m is preferably 1.

Accordingly, the preferred examples of the oxime ester compound of the present invention represented by general formula (I) include compounds No. 1 to No. 20 below, although the present invention is in no way limited to the compounds below.

[Chemical Formula 5]

Compound No. 1

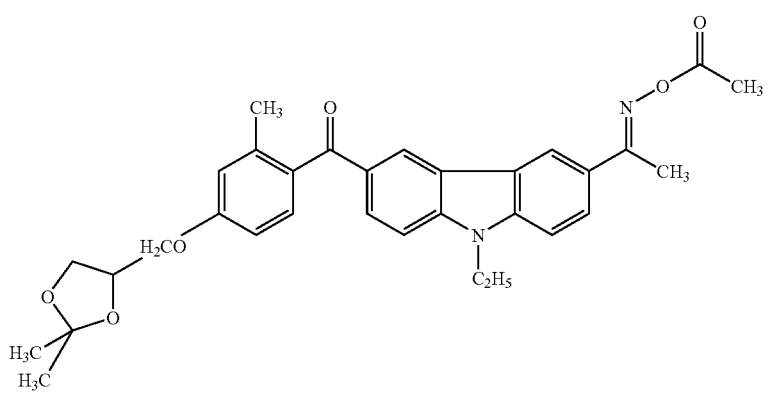

[Chemical Formula 6]

Compound No. 2

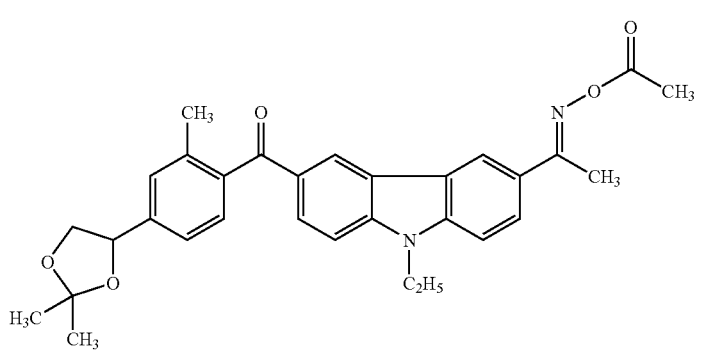

-continued
[Chemical Formula 7]
Compound No. 3
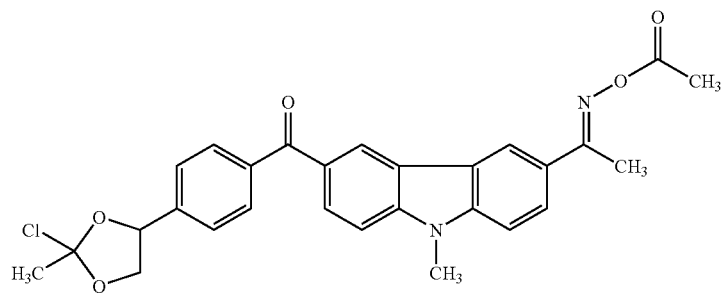
[Chemical Formula 8]
Compound No. 4
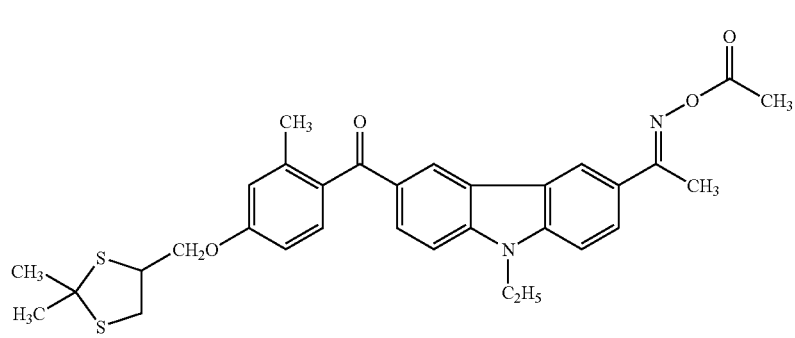
[Chemical Formula 9]
Compound No. 5
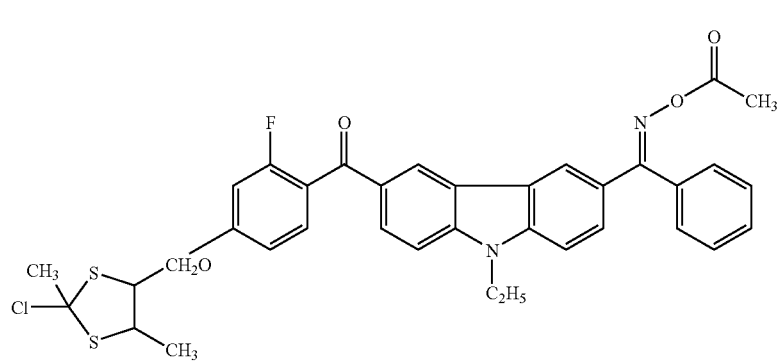
[Chemical Formula 10]
Compound No. 6
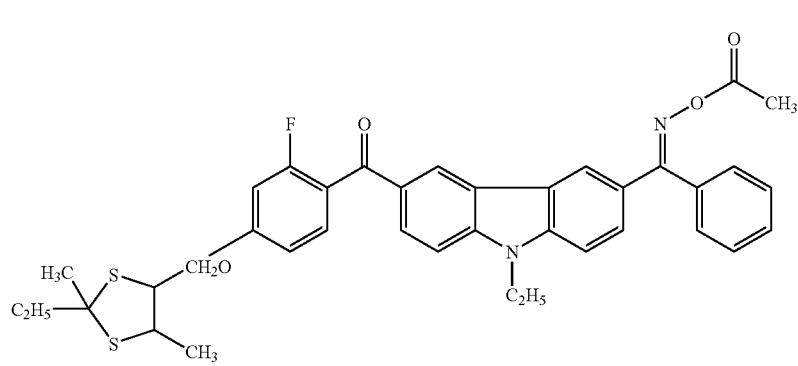

-continued
[Chemical Formula 11]
Compound No. 7
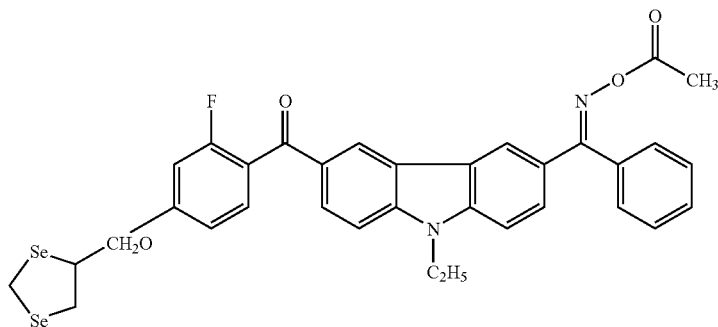
[Chemical Formula 12]
Compound No. 8
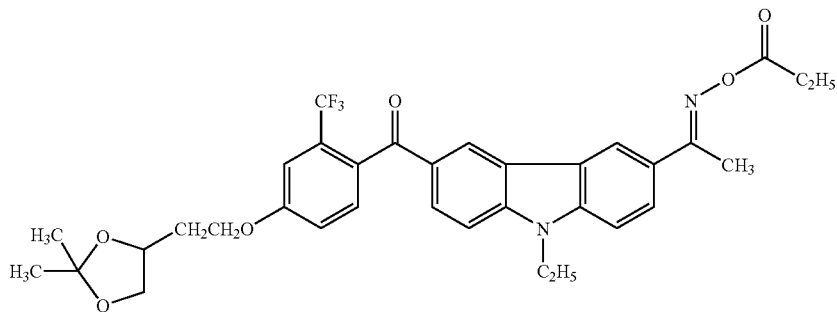
[Chemical Formula 13]
Compound No. 9
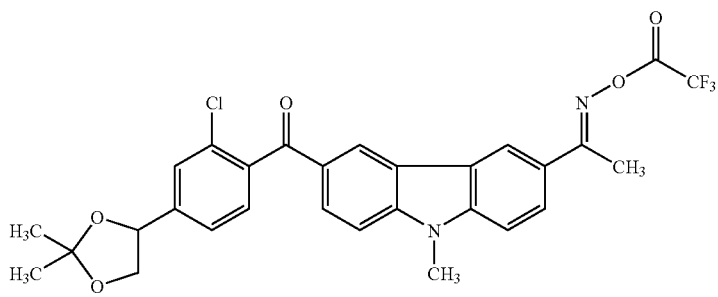
[Chemical Formula 14]
Compound No. 10
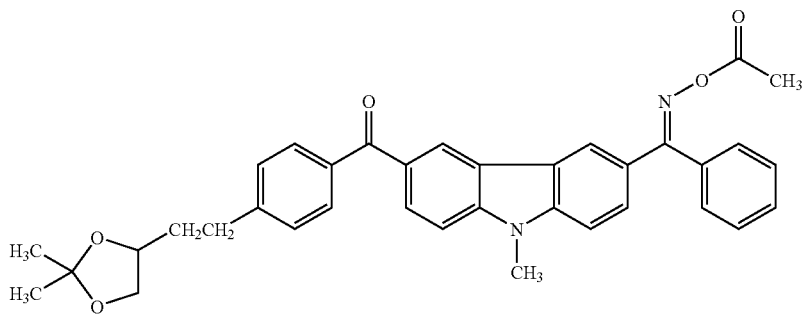

-continued
[Chemical Formula 15]
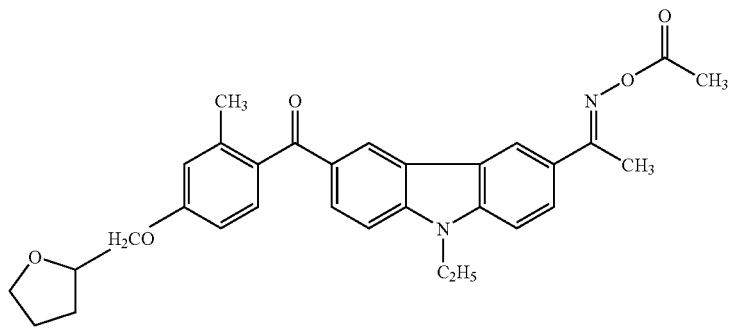
Compound No. 11
[Chemical Formula 16]
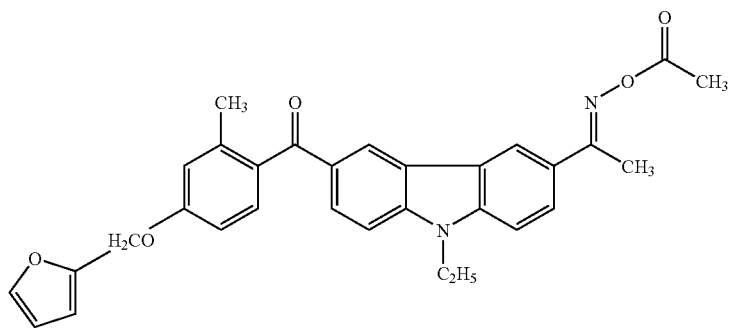
Compound No. 12
[Chemical formula 17]
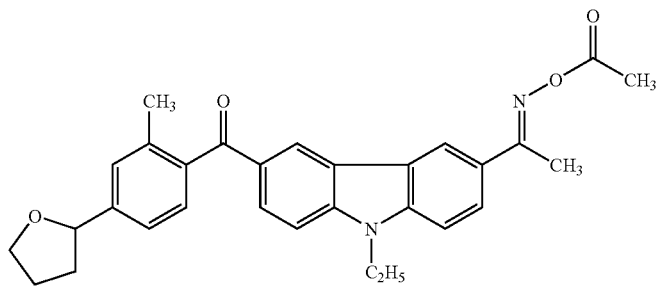
Compound No. 13
[Chemical formula 18]
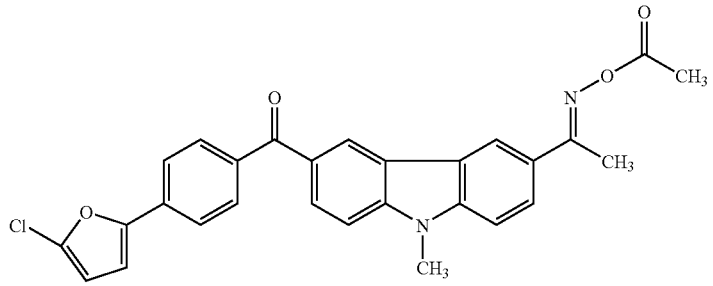
Compound No. 14

-continued
[Chemical formula 19]
Compound No. 15
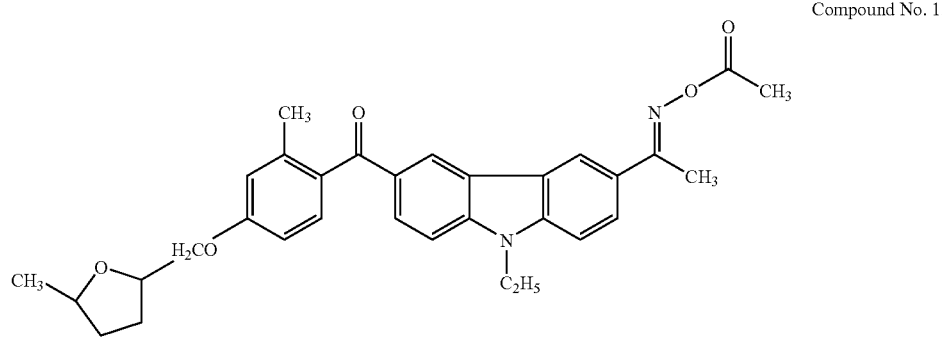
[Chemical formula 20]
Compound No. 16
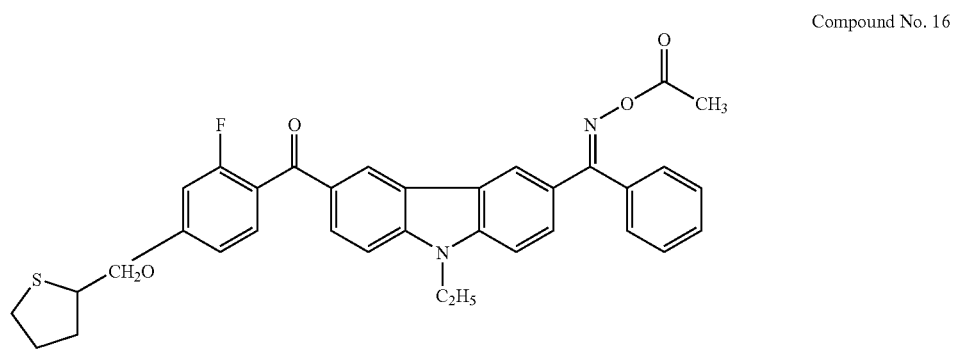
[Chemical Formula 21]
Compound No. 17
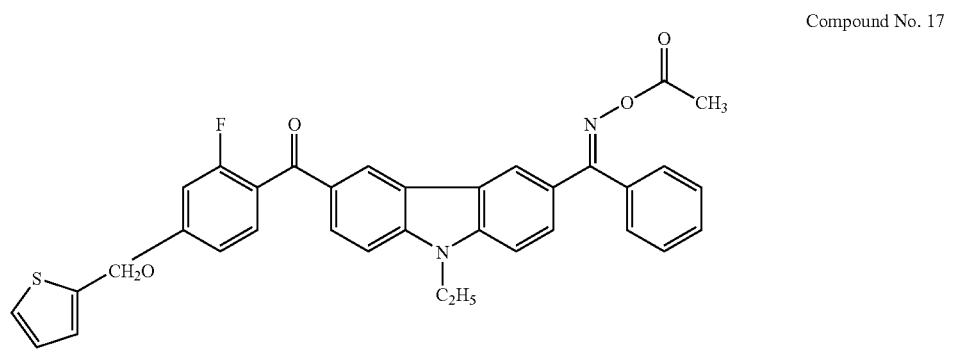
[Chemical Formula 22]
Compound No. 18
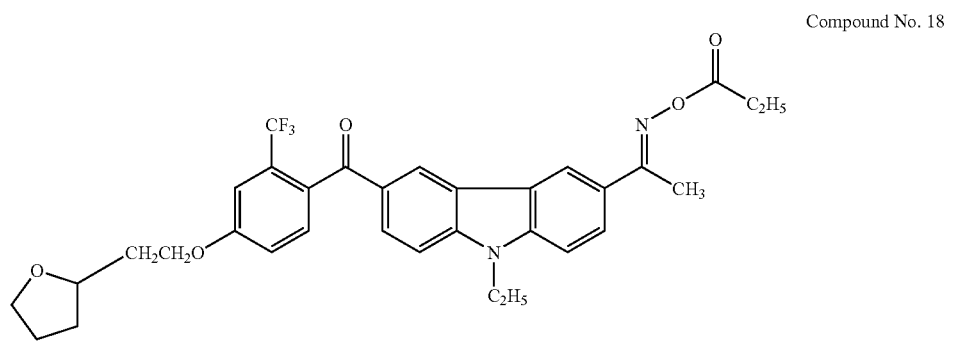

[Chemical Formula 23]

Compound No. 19

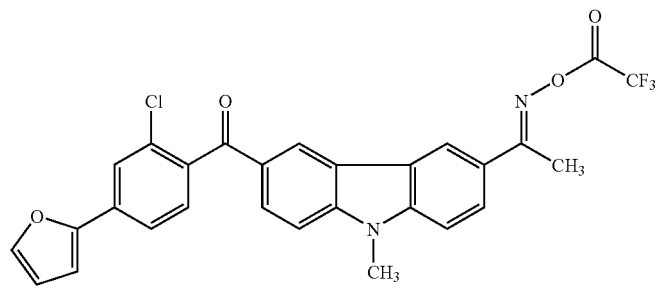

[Chemical Formula 24]

Compound No. 20

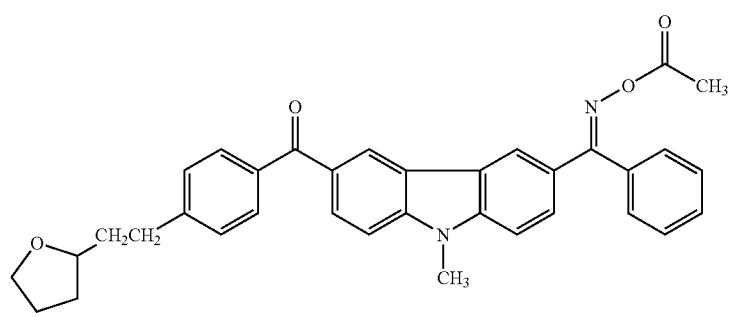

The method for synthesizing the oxime ester compound of the present invention represented by general formula (I) is not particularly limited. For example, the compound wherein $Y^1$ is an oxygen atom and q is 1 can be synthesized by the following method as shown below in the reaction scheme [Chemical Formula 25]. At first, carbazole compound 1 is reacted, simultaneously or sequentially, with acyl chloride 2 and acyl chloride 3 having a halogen atom as one of X in the presence of zinc chloride to obtain acyl compound 4, which is reacted with alcohol compound 5 in the presence of tetrabutylammonium hydrogensulfate to obtain acyl compound 6. Alternatively, alcohol compound 5 may be reacted with acyl chloride 3 prior to the acylation of carbazole compound 1. Next, acyl compound 6 is reacted with hydroxylamine hydrochloride to obtain oxime compound 7, which is reacted with acid anhydride 8 or acyl chloride 8' to obtain the oxime ester compound of the present invention represented by general formula (I). The oxime ester compound wherein $Y^1$ is a sulfur atom or a selenium atom and the compound with q of 0 can be also prepared according to the above method.

[Chemical Formula 25]

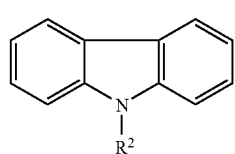

Carbazole 1

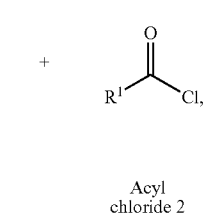

Acyl chloride 2

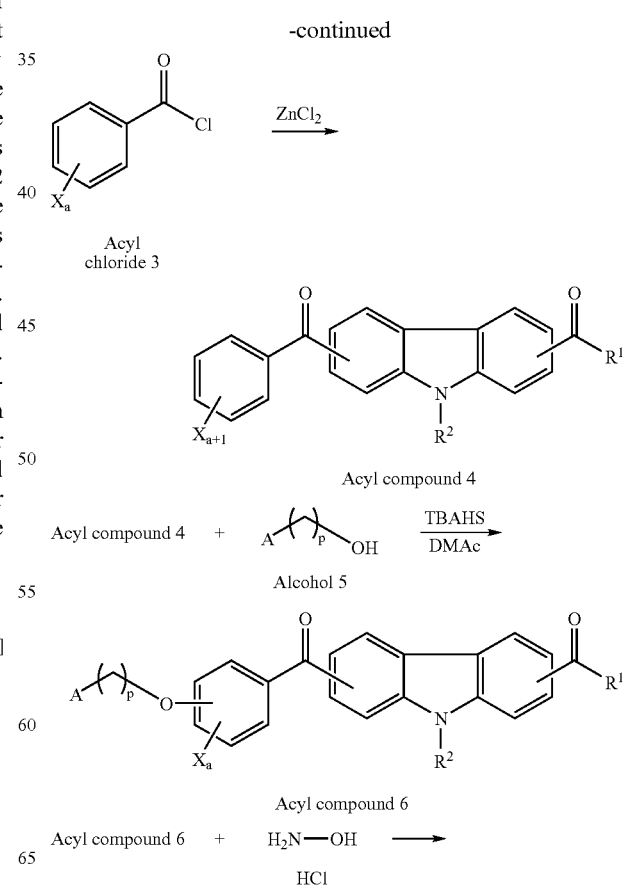

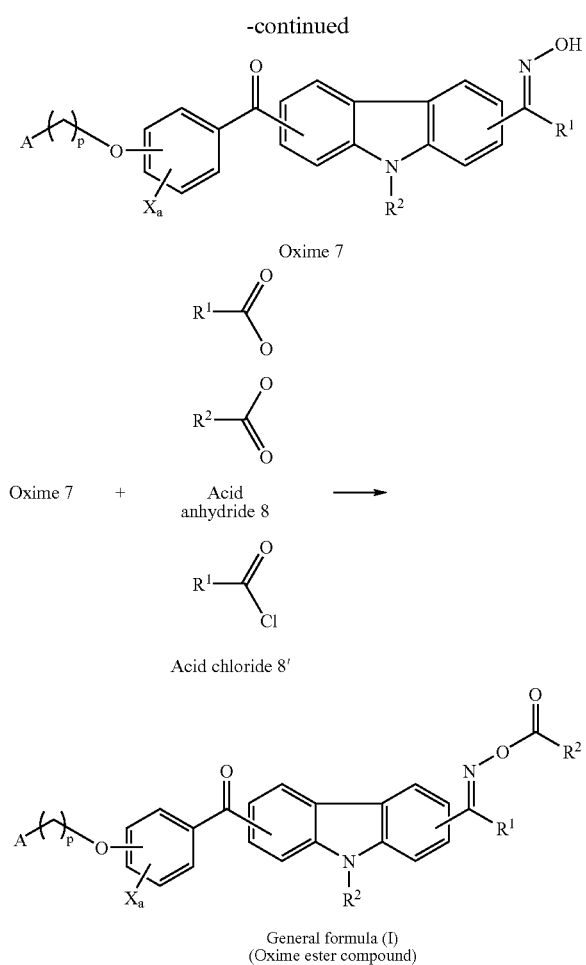

The oxime ester compound of the present invention is useful as a photopolymerization initiator for a polymerizable compound having (an) ethylenic unsaturated bond(s).

The photosensitive composition of the present invention will be described below.

The photosensitive composition of the present invention comprises adding a photopolymerization initiator which contains the oxime ester compound of the present invention as an active constituent to a polymerizable compound having (an) ethylenic unsaturated bond(s).

As the polymerizable compound having (an) ethylenic unsaturated bond(s), such compounds commonly used for photosensitive compositions may be used. That is, the polymerizable compound having (an) ethylenic unsaturated bond(s) includes, for example, an unsaturated monocarboxylic acid such as (meth)acrylic acid, crotonic acid, α-chloroacrylic acid, cinnamic acid, and sorbic acid; an unsaturated dicarboxylic acid or anhydride thereof such as maleic acid, maleic anhydride, fumaric acid, itaconic acid, itaconic anhydride, citraconic acid, citraconic anhydride, and mesaconic acid; an unsaturated polycarboxylic acid having three or more carboxyl groups such as trimellitic acid, pyromellitic acid, 2,2'-3,3'-benzophenonetetracarboxylic acid, and 3,3'-4,4'-benzophenonetetracarboxylic acid, and anhydride thereof; a mono[(meth)acryloyloxyalkyl]ester of a polycarboxylic acid having two or more carboxyl groups such as mono[(2-meth)acryloyloxyethyl]succinate and mono[(2-meth)acryloyloxyethyl]phthalate; an unsaturated mono basic acid like mono (meth)acrylate ester of a polymer having a carboxyl group at one end and a hydroxyl group at the other end such as ω-carboxypolycaprolactone mono(meth)acrylate; an aromatic vinyl compound such as styrene, α-methylstyrene, chlorostyrene, methoxystyrene, divinylbenzene, vinyltoluene, vinylbenzyl methyl ether, and vinylbenzyl glycidyl ether; indene or its derivative such as indene and 1-methylindene; a compound obtained by esterifying a (poly)alcohol with an α,β-unsaturated carboxylic acid such as methyl(meth)acrylate, ethyl(meth)acrylate, n-propyl(meth)acrylate, isopropyl (meth)acrylate, n-butyl(meth)acrylate, isobutyl(meth)acrylate, sec-butyl(meth)acrylate, tert-butyl(meth)acrylate, tetrahydrofuryl(meth)acrylate, 2-ethylhexyl(meth)acrylate, lauryl(meth)acrylate, stearyl(meth)acrylate, cyclohexyl (meth)acrylate, hydroxyethyl(meth)acrylate, phenoxyethyl (meth)acrylate, methoxyethyl(meth)acrylate, ethoxyethyl (meth)acrylate, poly(ethoxy)ethyl(meth)acrylate, propyloxyethyl(meth)acrylate, butoxyethyl(meth)acrylate, butoxyethoxyethyl(meth)acrylate, poly(propyloxy)propyl (meth)acrylate, vinyl(meth)acrylate, ethylene glycol di(meth)acrylate, diethylene glycol di(meth)acrylate, triethylene glycol di(meth)acrylate, polyethylene glycol di(meth) acrylate, propylene glycol di(meth)acrylate, polypropylene glycol di(meth)acrylate, 1,4-butanediol di(meth)acrylate, neopentylglycol di(meth)acrylate, 1,6-hexanediol di(meth) acrylate, trimethylolpropane tri(meth)acrylate, trimethylolethane tri(meth)acrylate, tris(2-acryloylethyl)isocyanurate, pentaerythritol penta(meth)acrylate, pentaerythritol tetra (meth)acrylate, allyl(meth)acrylate, and benzyl(meth)acrylate; an aminoalkyl ester of an unsaturated carboxylic acid such as 2-aminoethyl(meth)acrylate, 2-dimethylaminoethyl (meth)acrylate, 2-aminopropyl(meth)acrylate, 2-dimethylaminopropyl(meth)acrylate, 3-aminopropyl(meth)acrylate, and 3-dimethylaminopropyl(meth)acrylate; a glycidyl ester of an unsaturated carboxylic acid such as glycidyl(meth) acrylate; a vinyl ester of a carboxylic acid such as vinyl acetate, vinyl propionate, vinyl butyrate, and vinyl benzoate; an unsaturated ether such as vinyl methyl ether, vinyl ethyl ether, allyl glycidyl ether, and isobutyl vinyl ether; a cyanovinyl compound such as (meth)acrylonitrile, α-chloroacrylonitrile, and vinylidene cyanide; an unsaturated amide such as (meth)acrylamide, α-chloroacrylamide, N-2-hydroxyethyl (meth)acrylamide; an unsaturated imide such as maleimide, N-phenylmaleimide, and N-cyclohexylmaleimide; an aliphatic conjugated diene such as 1,3-butadiene, isoprene, and chloroprene; a macromolecular monomer having a mono (meth)acryloyl group at one end of the chain in a polymer molecule like polystyrene, polymethyl(meth)acrylate, poly-n-butyl(meth)acrylate, or polysiloxane; N-vinylpyrrolidone, vinyl chloride, vinylidene chloride, divinyl succinate, diallyl phthalate, triallyl phosphate, triallyl isocyanurate, and the like. These polymerizable compounds may be used alone, as a mixture of two or more, or as a (co)polymer prepared by pre-(co)polymerization.

In particular, the photopolymerization initiator containing the oxime ester compound of the present invention as an active constituent is suitably used for styrene, methyl(meth) acrylate, n-butyl(meth)acrylate, and hydroxyethyl(meth) acrylate.

In the photosensitive composition of the present invention, although the amount of photopolymerization initiator to be added is not limited, the amount of the oxime ester compound of the present invention is preferably 1 to 50 parts by mass, more preferably 5 to 30 parts by mass, with respect to 100 parts by mass of the above polymerizable compound having (an) ethylenic unsaturated bond(s).

To the photosensitive composition of the present invention, a colorant may be further added to form a colored photosensitive composition. The colorant includes a dye, a pigment, a natural pigment, and the like. These colorants may be used alone or as a mixture of two or more.

The pigment includes Pigment Red 1, 2, 3, 9, 10, 14, 17, 22, 23, 31, 38, 41, 48, 49, 88, 90, 97, 112, 119, 122, 123, 144, 149, 166, 168, 169, 170, 171, 177, 179, 180, 184, 185, 192, 200, 202, 209, 215, 216, 217, 220, 223, 224, 226, 227, 228, 240, and 254; Pigment Orange 13, 31, 34, 36, 38, 43, 46, 48, 49, 51, 52, 55, 59, 60, 61, 62, 64, 65, and 71; Pigment Yellow 1, 3, 12, 13, 14, 16, 17, 20, 24, 55, 60, 73, 81, 83, 86, 93, 95, 97, 98, 100, 109, 110, 113, 114, 117, 120, 125, 126, 127, 129, 137, 138, 139, 147, 148, 150, 151, 152, 153, 154, 166, 168, 175, 180, and 185; Pigment Green 7, 10, and 36; Pigment Blue 15, 15:1, 15:2, 15:3, 15:4, 15:5, 15:6, 22, 24, 56, 60, 61, 62, and 64; Pigment Violet 1, 19, 23, 27, 29, 30, 32, 37, 40, and 50; carbon black, Pigment Black 7, titanium black; and inorganic pigments such as titanium oxide, barium sulfate, calcium carbonate, magnesium carbonate, zinc oxide, lead sulfate, lead yellow, zinc yellow, red iron oxide (red iron oxide (III)), milori blue, cadmium red, ultramarine blue, iron blue, chromium oxide green, cobalt green, cobalt blue, artificial iron blue, umber, silica, alumina, and talc.

On preparing the colored photosensitive composition, the colorant is added in an amount of preferably 0.1 to 50 parts by mass, more preferably 0.5 to 20 parts by mass, with respect to 100 parts by mass of the polymerizable compound having (an) ethylenic unsaturated bond(s).

In the present invention, a monofunctional or polyfunctional epoxy compound may be used for adjusting acid value to obtain improved performances in development of the photosensitive composition of the present invention. The photosensitive composition of the present invention preferably has an acid value of its solid content in a range from 60 to 120 mg KOH/g, and the monofunctional or polyfunctional epoxy compound is preferably used in such an amount that the acid value of the resultant composition falls in this range.

The monofunctional epoxy compound includes glycidyl methacrylate, methyl glycidyl ether, ethyl glycidyl ether, propyl glycidyl ether, isopropyl glycidyl ether, butyl glycidyl ether, isobutyl glycidyl ether, tert-butyl glycidyl ether, pentyl glycidyl ether, hexyl glycidyl ether, heptyl glycidyl ether, octyl glycidyl ether, nonyl glycidyl ether, decyl glycidyl ether, undecyl glycidyl ether, dodecyl glycidyl ether, tridecyl glycidyl ether, tetradecyl glycidyl ether, pentadecyl glycidyl ether, hexadecyl glycidyl ether, 2-ethylhexyl glycidyl ether, allyl glycidyl ether, propargyl glycidyl ether, p-methoxyethyl glycidyl ether, phenyl glycidyl ether, p-methoxy glycidyl ether, p-butylphenyl glycidyl ether, cresyl glycidyl ether, 2-methylcresyl glycidyl ether, 4-nonylphenyl glycidyl ether, benzyl glycidyl ether, p-cumylphenyl glycidyl ether, trityl glycidyl ether, 2,3-epoxypropyl methacrylate, epoxidized soybean oil, epoxidized linseed oil, glycidyl butyrate, vinylcyclohexane monooxide, 1,2-epoxy-4-vinylcyclohexane, styrene oxide, pinene oxide, methylstyrene oxide, cyclohexene oxide, propylene oxide, compounds No. 21 and No. 22 below, and the like.

[Chemical Formula 26]

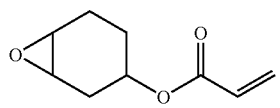

No. 21

[Chemical Formula 27]

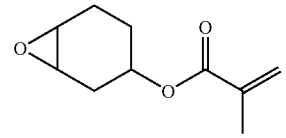

No. 22

As the polyfunctional epoxy compound, it is preferred to use one or more compounds selected from the group consisting of bisphenol-type epoxy compounds and glycidyl ethers because such compounds provide alkali-developing resin compositions or colored alkali-developing resin compositions with more excellent characteristics. As the bisphenol-type epoxy compound, there may be used, for example, an alkylidenebisphenol polyglycidyl ether-type epoxy compound such as bisphenol A glycidyl ether, bisphenol F glycidyl ether, and bisphenol Z glycidyl ether; a hydrogenated bisphenol-type epoxy compound, and the like. The glycidyl ether includes ethylene glycol diglycidyl ether, propylene glycol diglycidyl ether, 1,4-butanediol diglycidyl ether, 1,6-hexanediol diglycidyl ether, 1,8-octanediol diglycidyl ether, 1,10-decanediol diglycidyl ether, 2,2-dimethyl-1,3-propanediol diglycidyl ether, diethylene glycol diglycidyl ether, triethylene glycol diglycidyl ether, tetraethylene glycol diglycidyl ether, hexaethylene glycol diglycidyl ether, 1,4-cyclohexanedimethanol diglycidyl ether, 1,1,1-tri(glycidyloxymethyl)propane, 1,1,1-tri(glycidyloxymethyl)ethane, 1,1,1-tri(glycidyloxymethyl)methane, and 1,1,1,1-tetra(glycidyloxymethyl)methane.

There may be also used a novolak-type epoxy compound such as phenol novolak-type epoxy compound, biphenyl novolak-type epoxy compound, cresol novolak-type epoxy compound, bisphenol A novolak-type epoxy compound, and dicyclopentadiene novolak-type epoxy compound; an alicyclic epoxide such as 3,4-epoxy-6-methylcyclohexylmethyl 3,4-epoxy-6-methylcyclohexanecarboxylate, 3,4-epoxycyclohexylmethyl 3,4-epoxycyclohexanecarboxylate, and 1-epoxyethyl-3,4-epoxycyclohexane; a glycidyl ester such as diglycidyl phthalate, diglycidyl tetrahydrophthalate, and dimer acid glycidyl ester; a glycidylamine such as tetraglycidyidiaminodiphenylmethane, triglycidyl-p-aminophenol, and N,N-diglycidylaniline; a heterocycle-containing epoxy compound such as 1,3-diglycidyl-5,5-dimethylhidantoin and triglycidyl isocyanurate; a diepoxide such as dicyclopentadiene dioxide; naphthalene skeleton-containing epoxide, a triphenylmethane skeleton-containing epoxide; a dicyclopentadiene skeleton-containing epoxide, and the like.

Together with the polymerizable compound having (an) ethylenic unsaturated bond(s), another organic polymer may be used to improve characteristics of the cured material. Such an organic polymer includes, for example, polystyrene, polymethylmethacrylate, methyl methacrylate-ethyl acrylate copolymer, poly(meth)acrylic acid, styrene-(meth)acrylic acid copolymer, (meth)acrylic acid-methyl methacrylate copolymer, ethylene-vinyl chloride copolymer, ethylene-vinyl copolymer, polyvinyl chloride resin, ABS resin, nylon-6, nylon-66, nylon-12, urethane resin, polycarbonate, polyvinylbutyral, cellulose ester, polyacrylamide, saturated polyester, phenol resin, phenoxy resin, polyamideimide resin, polyamic acid resin, epoxy resin, and the like. Among these, polystyrene, (meth)acrylic acid-methyl acrylate copolymer, and epoxy resin are preferred. When these other organic polymers are used, the amount thereof is preferably 10 to 500 parts by mass with respect to 100 parts by mass of the polymerizable compound having (an) ethylenic unsaturated bond(s).

In the photosensitive composition of the present invention, there may be additionally used a monomer having an unsaturated bond, a chain transfer agent, a surfactant, or the like.

The monomer having an unsaturated bond includes, for example, 2-hydroxyethyl acrylate, 2-hydroxypropyl acrylate, isobutyl acrylate, n-octyl acrylate, isooctyl acrylate, isononyl acrylate, stearyl acrylate, methoxyethyl acrylate, dimethylaminoethyl acrylate, zinc acrylate, 1,6-hexanediol diacrylate, trimethylolpropane triacrylate, 2-hydroxyethyl methacrylate, 2-hydroxypropyl methacrylate, butyl methacrylate, tert-butyl methacrylate, cyclohexyl methacrylate, trimethylolpropane trimethacrylate, dipentaerythritol pentaacrylate, dipentaerythritol hexaacrylate, pentaerythritol tetraacrylate, pentaerythritol triacrylate, bisphenol A diglycidyl ether (meth)acrylate, bisphenol F diglycidyl ether(meth)acrylate, bisphenol Z diglycidyl ether(meth)acrylate, tripropylene glycol di(meth)acrylate, and the like.

The chain transfer agent includes a mercapto compound such as thioglycolic acid, thiomalic acid, thiosalicylic acid, 2-mercaptopropionic acid, 3-mercaptopropionic acid, 3-mercaptobutyric acid, N-(2-mercaptopropionyl)glycine, 2-mercaptonicotinic acid, 3-[N-(2-mercaptoethyl)carbamoyl]propionic acid, 3-[N-(2-mercaptoethyl)amino]propionic acid, N-(3-mercaptopropionyl)alanine, 2-mercaptoethanesulfonic acid, 3-mercaptopropanesulfonic acid, 4-mercaptobutanesulfonic acid, dodecyl(4-methylthio)phenyl ether, 2-mercaptoethanol, 3-mercapto-1,2-propanediol, 1-mercapto-2-propanol, 3-mercapto-2-butanol, mercaptophenol, 2-mercaptoethylamine, 2-mercaptoimidazole, 2-mercapto-3-pyridinol, 2-mercaptobenzothiazole, mercaptoacetic acid, trimethylolpropane tris(3-mercaptopropionate), and pentaerythritol tetrakis(3-mercaptopropionate); a disulfide obtained by oxidizing the mercapto compound; and an iodoalkyl-containing compound such as iodoacetic acid, iodopropionic acid, 2-iodoethanol, and 2-iodoethanesulfonic acid.

The surfactant includes a fluorosurfactant such as a perfluoroalkyl phosphate and a salt of perfluoroalkanoic acid; an anionic surfactant such as an alkali metal salt of a higher fatty acid, a salt of alkylsulfonic acid, and a salt of alkyl sulfate; a cationic surfactant such as a hydrohalide of higher amine and a quaternary ammonium salt; a nonionic surfactant such as polyethylene glycol alkyl ether, a fatty acid ester of polyethylene glycol, a fatty acid ester of sorbitane, and a fatty acid monoglyceride; an amphoteric surfactant; a silicone-based surfactant; and the like. These may be used in combination.

In the photosensitive composition of the present invention, another photopolymerization initiator may be optionally used together with the oxime ester compound of the present invention. The concomitant use of such another photopolymerization initiator may exert a remarkable synergic effect in some cases.

As the photopolymerization initiator that can be used together with the oxime ester compound of the present invention, there may be used a conventional photopolymerization initiator, which includes, for example, benzophenone, phenylbiphenyl ketone, 1-hydroxy-1-benzoylcyclohexane, benzoin, benzil dimethyl ketal, 1-benzyl-1-dimethylamino-1-(4'-morpholinobenzoyl)propane, 2-morpholyl-2-(4'-methylmercapto)benzoylpropane, thioxanthone, 1-chloro-4-propoxythioxanthone, isopropylthioxanthone, diethylthioxanthone, ethylanthraquinone, 4-benzoyl-4'-methyidiphenyl sulfide, benzoin butyl ether, 2-hydroxy-2-benzoylpropane, 2-hydroxy-2-(4'-isopropyl)benzoylpropane, 4-butylbenzoyltrichloromethane, 4-phenoxybenzoyldichloromethane, methyl benzoylformate, 1,7-bis(9'-acridinyl)heptane, 9-n-butyl-3,6-bis(2'-morpholinoisobutyroyl)carbazole, 2-methyl-4,6-bis(trichloromethyl)-s-triazine, 2-phenyl-4,6-bis(trichloromethyl)-s-triazine, 2-naphthyl-4,6-bis(trichloromethyl)-s-triazine, 2,2-bis(2-chlorophenyl)-4,5,4',5'-tetraphenyl-1,2'-biimidazole, 4,4-azobisisobutyronitrile, triphenylphosphine, camphorquinone, N-1717 (available from Asahi Denka Co., Ltd.), benzoin peroxide, compounds No. 23 and No. 24 below, and the like. These photopolymerization initiators may be used alone or in a combination of two or more. When these other photopolymerization initiators are used, the amount thereof is preferably equal to or smaller than the amount of the oxime ester compound of the present invention.

[Chemical Formula 28]

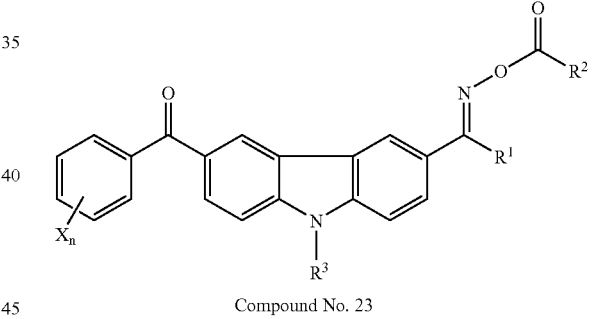

Compound No. 23

(In the formula, $R^1$, $R^2$, $R^3$, and X are the same as those in general formula (I) and n is an integer of 0 to 5.)

[Chemical Formula 29]

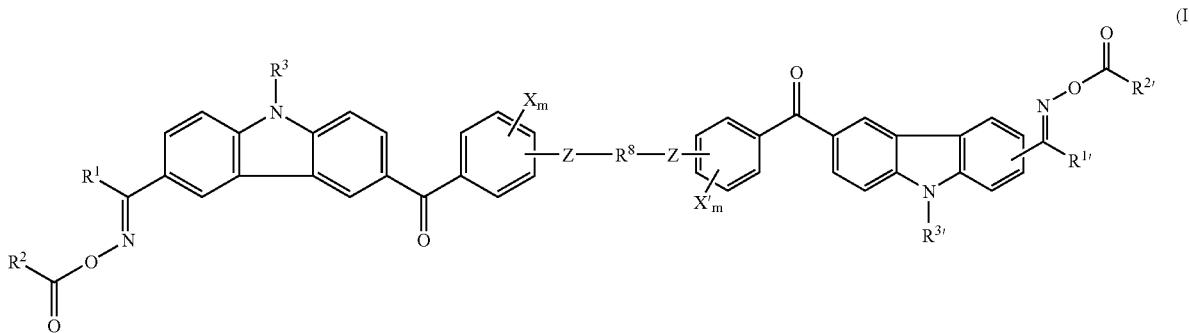

Compound No. 24

(In the formula, $R^1$, $R^2$, $R^3$, X, and m are the same as those in general formula (I); $R^{1'}$, $R^{2'}$, $R^{3'}$, and X' represent the same atom or group as $R^1$, $R^2$, $R^3$, and X in general formula (I), respectively; $R^8$ represents a diol residue or a dithiol residue; and Z represents an oxygen atom or a sulfur atom.)

To the photosensitive composition of the present invention, there may be optionally added a conventional additive, which includes a thermal polymerization inhibitor such as p-anisol, hydroquinone, pyrocatecol, tert-butylcatecol, and phenothiazine; a plasticizer; an adhesion improver; a filler; an antifoaming agent; a leveling agent; a surface modifier; an antioxidant; a UV absorber; a dispersion aid; an aggregation inhibitor; a catalyst; a promoter; a photosensitizer; a crosslinking agent; and the like.

In the photosensitive composition of the present invention, there are no particular limitations on the amounts of compounds (excluding the above-described other photopolymerization initiator, the colorant, and a solvent described later) optionally used other than the polymerizable compound having (an) ethylenic unsaturated bond(s) or the oxime ester compound of the present invention. Although these compounds may be used in an amount appropriately determined according to the purpose of use, the total amount thereof is preferably parts by mass or less with respect to 100 parts by mass of the polymerizable compound having (an) ethylenic unsaturated bond(s).

To the photosensitive composition of the present invention, there is usually added a solvent that can dissolve or disperse the above-described constituents (the oxime ester compound of the present invention, the polymerizable compound having (an) ethylenic unsaturated bond(s), etc.) as necessary. The solvent includes, for example, ketones such as methyl ethyl ketone, methyl amyl ketone, diethyl ketone, acetone, methyl isopropyl ketone, methyl isobutyl ketone, and cyclohexanone; ethers such as ethyl ether, dioxane, tetrahydrofuran, 1,2-dimethoxyethane, 1,2-diethoxyethane, and dipropylene glycol dimethyl ether; esters such as methyl acetate, ethyl acetate, n-propyl acetate, isopropyl acetate, and n-butyl acetate; cellosolves such as ethylene glycol monomethyl ether(methyl cellosolve), ethylene glycol monoethyl ether (ethyl cellosolve), and propylene glycol monomethyl ether acetate; alcohols such as methanol, ethanol, isopropanol, n-propanol, isobutanol, n-butanol, and amyl alcohol; BTX compounds such as benzene, toluene, and xylene; aliphatic hydrocarbons such as hexane, heptane, octane, and cyclohexane; terpene-type hydrocarbon oils such as terpine oil, D-limonene, and pinene; paraffins such as mineral spirit, Swasol #310 (Cosmo Matsuyama Oil Co., Ltd.), and Solvesso #100 (Exxon); halogenated aliphatic hydrocarbons such as carbon tetrachloride, chloroform, trichloroethylene, and methylene dichloride; aryl halides such as chlorobenzene; carbitols, aniline, triethylamine, pyridine, acetic acid, acetonitrile, carbon disulfide, N,N-dimethylformamide, N-methylpyrrolidone, and the like. Among these, ketones and cellosolves are preferred. These solvents may be used alone or as a mixture of two or more.

The photosensitive composition of the present invention can be applied onto a supporting base made of soda glass, quartz glass, semiconductor substrate, metal, paper, plastics, or the like by a publicly known process such as spin-coating, roll-coating, bar-coating, die-coating, curtain-coating, various type of printing, and dipping. It is also possible that the composition is once applied onto a supporting base such as a film and then transcribed onto another supporting base. There are no limitations on the method of applying the composition.

The photosensitive composition of the present invention can be used for various use such as photocurable paints, photocurable inks, photocurable adhesive agents, printing plates, photoresists for printed wiring boards, printed circuit boards, and color display elements for liquid crystal displays in color television sets, PC monitors, portable information terminals, digital cameras, or the like. There are no limitations on the use of the composition.

As an excitation light source used for curing the photosensitive composition comprising the oxime ester compound of the present invention, there may be used a light source emitting light in the wavelength range of 300 to 450 nm, which is exemplified by a super-high pressure mercury lamp, a mercury vapor arc, a carbon arc, a xenon arc, and the like.

EXAMPLES

The present invention will be described in more detail with reference to Examples, but the present invention is not limited thereto.

Example 1

Production of Compound No. 1

<Step 1> Production of 4-fluoro-2-methylbenzoyl chloride

4-Fluoro-2-methylbenzoyl chloride (structure is shown in [Chemical Formula 30] below) was produced by the following procedures.

[Chemical Formula 30]

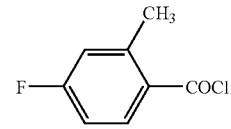

Under nitrogen atmosphere, 20.0 g (0.13 mol) of 4-fluoro-2-methylbenzoic acid, 0.10 g (1.3 mmol) of N,N-dimethylformamide, and 134 g of toluene were charged, and 23.2 g (0.20 mol) of thionyl chloride was added here dropwise at room temperature. The mixture was heated to 60 to 65° C. and stirred for 1 hr. The solvent was distilled off, and the residue was dried under vacuum at 50° C. to obtain 19.7 g of a brown liquid (Yield 88%; Purity 99%, determined by GC).

The resultant brown liquid was confirmed to be the desired product from the measured IR spectral data shown below.

IR (cm$^{-1}$): 2985, 2931, 1766, 1606, 1579, 1486, 1450, 1384, 1240, 1189, 1105, 964, 869, 823.

<Step 2> Production of the Acyl Compound

The acyl compound shown in [Chemical Formula 31] below was produced by the following procedures.

[Chemical Formula 31]

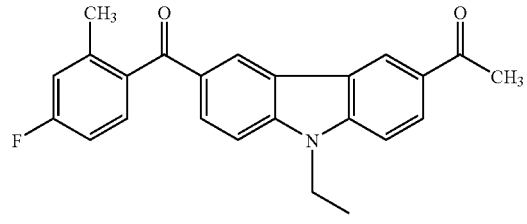

Acyl compound

A mixture of 33.1 g of monochlorobenzene, 21.5 g (0.11 mol) of N-ethylcarbazole, and 1.40 g (10 mmol) of zinc chloride was heated at 80° C., and here was added dropwise 17.3 g (0.10 mol) of 4-fluoro-2-methylbenzoyl chloride obtained in Step 1. The resultant mixture was stirred at 80 to 85° C. for 1 hr, and then cooled to room temperature. To the reaction mixture, 33.1 g of n-heptane and 16.5 g of water were added and the organic layer was collected. The organic layer was neutralized by adding 8.30 g of aqueous solution containing 1% of sodium hydroxide, and 40.0 g of water was added here in two portions for washing the organic layer. From the collected organic layer, n-heptane was distilled off to obtain 50.0 g of a monochlorobenzene solution. To the resultant monochlorobenzene solution, 90.0 g of monochlorobenzene was added dropwise, 40.0 g of aluminum chloride was added here, and the mixture was cooled to 10 to 15° C. To this mixture, 9.90 g (0.13 mol) of acetyl chloride was added dropwise at 10 to 20° C., and the resultant mixture was stirred at room temperature for 1 hr. The reaction solution was dropped into a mixture of 224 g of dichloroethane and 134 g of ice-water at 25 to 30° C. The organic layer was collected and washed with 40 g of 5% hydrochloric acid, 40 g of water, and 40 g of 2% aqueous NaOH solution in this order. Dichloroethane was distilled off, and the residue was recrystallized from 74.6 g of n-propyl acetate. The precipitate was collected by filtration and washed with a mixed solvent of n-propyl acetate and n-heptane to obtain 22.4 g of a light yellow solid (Yield 60%; Purity 98%, determined by HPLC).

The light yellow crystalline product had a melting point of 175° C., and it was confirmed to be the desired acyl compound based on the $^1$H-NMR chemical shift data and IR spectral data shown below.

$^1$H-NMR (ppm)

8.70 (s, 1H), 8.52 (s, 1H), 8.17 (d, 1H), 8.09 (d, 1H), 7.50 (s, 1H), 7.48 (d, 1H), 7.39 (d, 1H), 7.05 (d, 1H), 7.00 (d, 1H), 4.45 (d, 2H), 2.73 (s, 3H), 2.37 (s, 3H) 1.49 (t, 3H).

IR (cm$^{-1}$)

3448, 3054, 2064, 1662, 1625, 1589, 1567, 1484, 1386, 1305, 1245, 1153, 1124, 1022, 809.

<Step 3> Production of Compound No. 1

Under nitrogen gas flow, 541 g (1.45 mol) of the acyl compound obtained in Step 2, 383 g (2.90 mol) of 2,2-dimethyl-1,3-dioxolane-4-methanol, 98.5 g (0.290 mol) of tetrabutylammonium hydrogensulfate, and 2.11 kg of dimethylacetamide were charged, and here was added 145 g (3.63 mol) of sodium hydroxide at 25 to 30° C. The mixture was stirred at 60° C. for 3 hr. After the reaction mixture was cooled to room temperature, 161 g (2.32 mol) of hydroxylamine hydrochloride was added here, and the resultant mixture was stirred at 80° C. for 2 hr and then cooled to 50° C. Here were added 1.45 kg of butyl acetate and 1.45 kg of water, and the organic layer was collected and washed with 1.45 kg of 5% aqueous sodium chloride solution. The organic layer was refluxed at 80 to 90° C. for 4 hr to remove water, 787 g of butyl acetate and 178 g (1.74 mol) of acetic anhydride were added here, and the resultant mixture was stirred at 83 to 85° C. for 2 hr. The reaction mixture was cooled to room temperature, 1.39 kg of 5% aqueous sodium hydroxide solution was added here, and the organic layer was collected and washed using 1.57 kg of water in two portions. The organic layer was filtered, the solvent was distilled off, and the residue was crystallized from a mixed solvent consisting of 1.42 kg of butyl acetate and 779 g of butyl ether. The crystalline substance was collected by filtration and dried to obtain 562 g of a colorless crystalline substance (Yield 71.4%; Purity 99.4%, determined by HPLC). Analytical data of the colorless crystalline substance confirmed that this substance was the desired product, compound No. 1. The data of analyses are shown below.

(Analytical Data)

(1) Melting point: 123° C.

(2) $^1$H-NMR (ppm): 8.5-6.8 (aromatic, 9H), 4.6 (m, 1H), 4.4 (q, 2H), 4.2 (m, 1H), 4.1 (m, 1H), 4.0 (m, 1H), 2.5 (s, 3H), 2.4 (s, 3H), 2.3 (s, 3H), 1.5 (s, 3H), 1.4 (s, 6H).

(3) IR (cm$^{-1}$): 2981, 2932, 1751, 1650, 1627, 1591, 1570, 1488, 1459, 1375, 1276, 1239, 1215, 1152, 1129, 1050, 894, 849, 810, 773.

(4) UV spectrum (acetonitrile:water=7:3): $\lambda_{max}$=268, 292, 332 nm (5) Decomposition temperature (temperature at 5% weight loss measured under nitrogen atmosphere at a heating rate of 10° C./min): 298° C.

Example 2

Production of Compound No. 11

Under nitrogen gas flow, 102.1 g (1.0 mol) of tetrahydrofurfuryl alcohol and 91.0 g of 1,3-dimethyl-2-imidazolidinone (DMI) were charged, and here was added 33.7 g (0.30 mol) of potassium t-butoxide at 30 to 40° C. The mixture was heated at 75° C., and 74.7 g (0.20 mol) of the acyl compound obtained in Step 2 of Example 1 and 182 g of DMI were added to this mixture over 5 min. At this time the temperature of the mixture rose to 80° C. After the mixture was stirred at 80° C. for 1 hr, 25.0 g (0.36 mol) of hydroxylamine hydrochloride was added here, and the resultant mixture was stirred at 80° C. for 40 min. The reaction mixture was cooled to room temperature, and 190 g of n-propyl acetate and 95 g of 4% aqueous potassium hydroxide solution were added and further 95 g of water were added here to separate an organic layer. The organic layer was washed using 190 g of water in two portions, subsequently washed with 95 g of 2% aqueous potassium hydroxide solution and further washed with 95 g of water. The organic layer was collected and refluxed at 80 to 90° C. over 2 hr to remove water. To the organic layer, 102 g of propyl acetate and 24.5 g (0.24 mol) of acetic anhydride were added, and the resultant solution was stirred at 80° C. for 20 min. The reaction solution was cooled to room temperature, the solvent was distilled off, and the residue was crystallized from a mixed solvent consisting of 120 g of propyl acetate and 50 g of heptane. The precipitate was collected by filtration and dried to obtain 19.9 g of a colorless crystalline substance (Yield 19%; Purity 99.6%, determined by HPLC). The analytical data of the colorless crystalline substance showed that this substance was the desired product, compound No. 11. The analytical data are shown below.

(Analytical Data)

(1) Melting point: 119.3° C.

(2) $^1$H-NMR (ppm): 8.48 (d, 1H), 8.43 (d, 1H), 8.08 (dd, 1H), 7.99 (dd, 1H), 7.46 (d, 1H), 7.44 (d, 1H), 7.37 (d, 1H), 6.90 (d, 1H), 6.82 (dd, 1H), 4.45-4.40 (q, 2H), 4.36-4.30 (m, 1H), 4.06 (dd, 2H), 4.00-3.95 (m, 1H), 3.90-3.84 (m, 1H), 2.52 (s, 3H), 2.39 (s, 3H), 2.30 (s, 3H), 2.18-1.94 (m, 3H), 1.86-1.77 (m, 1H), 1.48 (t, 3H)

(3) IR (cm$^{-1}$): 2972, 2872, 1752, 1644, 1626, 1590, 1487, 1453, 1375, 1309, 1276, 1239, 1176, 1145, 1129, 1082, 1036, 1009, 982, 931, 895, 823, 810, 773, 722

(4) UV spectrum (acetonitrile:water=9:1): $\lambda_{max}$=273, 299, 341 nm (5) Decomposition temperature (temperature at 5% weight loss measured under nitrogen atmosphere at a heating rate of 10° C./min): 306.5° C.

Example 3

Production of Compound No. 12

Under nitrogen gas flow, 15.7 g (0.16 mol) of furfuryl alcohol, 4.5 g (0.040 mol) of potassium t-butoxide, and 4.7 g of dimethylacetamide (DMAc) were charged and the mixture was heated to 75 to 80° C. To this mixture, 8.0 g (0.020 mol) of the acyl compound obtained in Step 2 of Example 1 and 18.7 g of DMAc were added over 30 min. After stirring at 75 to 80° C. for 1 hr, the mixture was cooled to 30° C., here were added 1.1 g (0.010 mol) of potassium t-butoxide and 1.9 g (0.028 mol) of hydroxylamine hydrochloride, and the resultant mixture was stirred at 95 to 100° C. for 1 hr. The reaction mixture was cooled to room temperature, and 10 g of n-butyl acetate and 20 g of water were added three times to separate an organic layer. The organic layer was dried over magnesium sulfate, 2.5 g (0.024 mol) of acetic anhydride was added to this solution, and the resultant solution was stirred at 80 to 85° C. for 1 hr. To the reaction mixture, 40 g of dibutyl ether was added. The resultant crystalline substance was filtered, washed with 5 g of dibutyl ether, and dried to obtain 7.4 g of a colorless crystalline substance (Yield 72%; Purity 98.9%, determined by HPLC).

The analytical data of the obtained colorless crystalline substance confirmed that this substance was the desired product, compound No. 12. The analytical data are shown below.

(Analytical Data)

(1) Melting point: 163.8° C.

(2) $^1$H-NMR (ppm): 8.50 (d, 1H), 8.44 (d, 1H), 8.08 (dd, 1H), 7.99 (dd, 1H), 7.48 (dd, 1H), 7.46 (d, 1H), 7.44 (d, 1H), 7.38 (d, 1H), 6.96 (d, 1H), 6.89 (dd, 1H), 6.49 (d, 1H), 6.42 (dd, 1H), 5.09 (s, 1H), 4.42 (q, 2H), 2.51 (s, 3H), 2.40 (s, 3H), 2.29 (s, 3H), 1.48 (t, 3H)

(3) IR (cm$^{-1}$): 2979, 2933, 1769, 1650, 1627, 1595, 1570, 1488, 1451, 1374, 1317, 1273, 1238, 1206, 1177, 1150, 1129, 1102, 1078, 1019, 995, 933, 883, 812, 790, 772, 758, 716, 703

(4) UV spectrum (acetonitrile:water=9:1): $\lambda_{max}$=273, 297, 341 nm (5) Decomposition temperature (temperature at 5% weight measured loss under nitrogen atmosphere at a heating rate of 10° C./min): 318.5° C.

Example 4

Production of Photosensitive Composition No. 1

To 14 g of an acrylic copolymer, 5.9 g of trimethylolpropane triacrylate, 2.7 g of compound No. 1 obtained in Example 1, and 79 g of ethyl cellosolve were added, and the mixture was well stirred to obtain photosensitive composition No. 1.

The above acrylic copolymer was obtained as follows: 20 parts by mass of methacrylic acid, 15 parts by mass of hydroxyethyl methacrylate, 10 parts by mass of methyl methacrylate, and 55 parts by mass of butyl methacrylate were dissolved to 300 parts by mass of ethyl cellosolve, and the polymerization was initiated under nitrogen atmosphere by adding 0.75 part by mass of azobisisobutyronitrile and allowed to proceed at 70° C. for 5 hr.

Example 5

Production of Photosensitive Composition No. 2

To 7.2 g of the same acrylic copolymer as that used in Example 4, 4.3 g of trimethylolpropane triacrylate, 2.0 g of compound No. 1 obtained in Example 1, and 87 g of ethyl cellosolve were added, and the mixture was well stirred to obtain photosensitive composition No. 2.

Example 6

Production of Photosensitive Composition No. 3

To 14 g of a styrene-acrylic photosensitive copolymer, 6.0 g of dipentaerythritol hexaacrylate, 1.3 g of compound No. 1 obtained in Example 1, 1.3 g of 2,2-bis(2-chlorophenyl)-4,5, 4',5'-tetraphenyl-1,2'-biimidazole, and 83 g of ethyl cellosolve were added, and the mixture was well stirred to obtain photosensitive composition No. 3.

The above styrene-acrylic photosensitive copolymer was obtained as follows: 26.3 parts by mass of styrene, 43.8 parts by mass of 2-hydroxy methacrylate, 35 parts by mass of methacrylic acid, and 70 parts by mass of ethyl methacrylate were dissolved to 175 parts by mass of ethyl cellosolve; the polymerization was initiated under nitrogen atmosphere by adding 0.75 part by mass of azobisisobutyronitrile and allowed to proceed at 90° C. for 5 hr; here was added, dropwise over ca. 10 min, a solution containing 23.5 parts by mass of isocyanatoethyl methacrylate and 0.11 part by mass of tin octanoate in 20 parts by mass of ethyl cellosolve; and the mixture was allowed to react for 2 hr.

Example 7

Production of Photosensitive Composition No. 4

To 12 g of the same styrene-acrylic photosensitive copolymer as that used in Example 6, 8.1 g of dipentaerythritol penta- or hexaacrylate, 2.5 g of compound No. 1 obtained in Example 1, 47 g of ethyl cellosolve, and 30 g of cyclohexanone were added, and the mixture was well stirred to obtain photosensitive composition No. 4.

Example 8

Production of Photosensitive Composition No. 5

To 20 g of the same acrylic photosensitive copolymer as that used in Example 4, 8.7 g of trimethylolpropane triacrylate, 2.2 g of compound No. 1 obtained in Example 1, 4.6 g of bisphenol A-type epoxy resin, and 65 g of ethyl cellosolve were added, and the mixture was well stirred to obtain photosensitive composition No. 5.

Example 9

Production of Photosensitive Composition No. 6

To 14 g of the same acrylic copolymer as that used in Example 4, 5.9 g of trimethylolpropane triacrylate, 2.7 g of compound No. 11 obtained in Example 2, and 79 g of ethyl cellosolve were added, and the mixture was well stirred to obtain photosensitive composition No. 6.

Example 10

Production of Photosensitive Composition No. 7

To 7.2 g of the same acrylic copolymer as that used in Example 4, 4.3 g of trimethylolpropane triacrylate, 2.0 g of compound No. 11 obtained in Example 2, and 87 g of ethyl cellosolve were added, and the mixture was well stirred to obtain photosensitive composition No. 7.

Example 11

Production of Photosensitive Composition No. 8

To 14 g of the same styrene-acrylic photosensitive copolymer as that used in Example 6, 6.0 g of dipentaerythritol hexaacrylate, 1.3 g of compound No. 11 obtained in Example 2, 1.3 g of 2,2-bis(2-chlorophenyl)-4,5,4',5'-tetraphenyl-1,2'-biimidazole, and 83 g of ethyl cellosolve were added, and the mixture was well stirred to obtain photosensitive composition No. 8.

Example 12

Production of Photosensitive Composition No. 9

To 12 g of the same styrene-acrylic photosensitive copolymer as that used in Example 6, 8.1 g of dipentaerythritol penta- or hexaacrylate, 2.5 g of compound No. 11 obtained in Example 2, 47 g of ethyl cellosolve, and 30 g of cyclohexanone were added, and the mixture was well stirred to obtain photosensitive composition No. 9.

Example 13

Production of Photosensitive Composition No. 10

To 20 g of the same acrylic copolymer as that used in Example 4, 8.7 g of trimethylolpropane triacrylate, 2.2 g of compound No. 11 obtained in Example 2, 4.6 g of bisphenol A-type epoxy resin, and 65 g of ethyl cellosolve were added, and the mixture was well stirred to obtain photosensitive composition No. 10.

Example 14

Production of Photosensitive Composition No. 11

To 14 g of the same acrylic copolymer as that used in Example 4, 5.9 g of trimethylolpropane triacrylate, 2.7 g of compound No. 12 obtained in Example 3, and 79 g of ethyl cellosolve were added, and the mixture was well stirred to obtain photosensitive composition No. 11.

Comparative Example 1

Production of Photosensitive Composition No. 12

To 14 g of the same acrylic copolymer as that used in Example 4, 5.9 g of dipentaerythritol penta- or hexaacrylate, 2.1 g of comparative compound No. 1 [decomposition temperature (temperature at 5% weight loss measured under nitrogen atmosphere at a heating rate of 10° C./min): 242.1° C.] represented by [Chemical Formula 32] below, and 78 g of ethyl cellosolve were added, and the mixture was well stirred to obtain photosensitive composition No. 12.

[Chemical Formula 32]

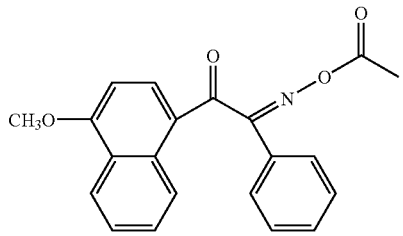

Comparative Example 2

Production of Photosensitive Composition No. 13

Photosensitive composition No. 13 was obtained under the same conditions as those in Comparative Example 1 except for using the same styrene-acrylic photosensitive copolymer as that used in Example 6 instead of the acrylic copolymer.

Comparative Example 3

Production of Photosensitive Composition No. 14

To 7.2 g of the same acrylic copolymer as that used in Example 4, 4.3 g of trimethylolpropane triacrylate, 1.5 g of comparative compound No. 2 [decomposition temperature (temperature at 5% weight loss measured under nitrogen atmosphere at a heating rate of 10° C./min): 232.2° C.] represented by [Chemical Formula 33] below, and 87 g of ethyl cellosolve were added, and the mixture was well stirred to obtain photosensitive composition No. 14.

[Chemical Formula 33]

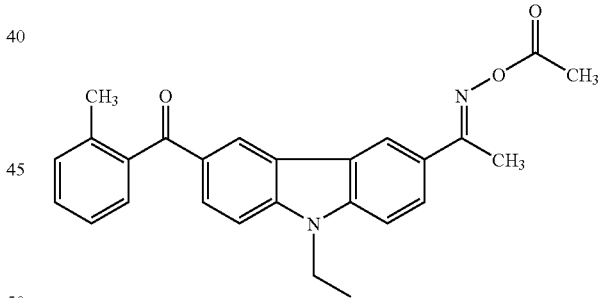

Comparative Example 4

Production of Photosensitive Composition No. 15

Photosensitive composition No. 15 was obtained under the same conditions as those in Comparative Example 3 except for using the same styrene-acrylic photosensitive copolymer as that used in Example 6 instead of the acrylic copolymer.

Example 15

Production of Colored Photosensitive Composition No. 1

To 12 g of the same acrylic copolymer as that used in Example 4, 8 g of trimethylolpropane triacrylate, 2.7 g of compound No. 1 obtained in Example 1, 1.0 g of Pigment Blue 15, and 79 g of ethyl cellosolve were added, and the mixture was well stirred to obtain colored photosensitive composition No. 1.

Example 16

Production of Colored Photosensitive Composition No. 2

To 6.9 g of the same acrylic copolymer as that used in Example 4, 4.3 g of trimethylolpropane triacrylate, 2.0 g of compound No. 1 obtained in Example 1, 1.0 g of Pigment Red 254, and 87 g of ethyl cellosolve were added, and the mixture was well stirred to obtain colored photosensitive composition No. 2.

Example 17

Production of Colored Photosensitive Composition No. 3

To 12 g of the same styrene-acrylic photosensitive copolymer as that used in Example 6, 4.0 g of dipentaerythritol hexaacrylate, 1.3 g of compound No. 1 obtained in Example 1, 1.3 g of 2,2-bis(2-chlorophenyl)-4,5,4',5'-tetraphenyl-1,2'-biimidazole, 0.7 g of Pigment Red 254, 0.3 g of Pigment Yellow 138, and 83 g of ethyl cellosolve were added, and the mixture was well stirred to obtain colored photosensitive composition No. 3.

Example 18

Production of Colored Photosensitive Composition No. 4

To 12 g of the same styrene-acrylic photosensitive copolymer as that used in Example 6, 6.1 g of dipentaerythritol penta- or hexaacrylate, 2.5 g of compound No. 1 obtained in Example 1, 3.2 g of carbon black, 47 g of ethyl cellosolve, and 30 g of cyclohexanone were added, and the mixture was well stirred to obtain colored photosensitive composition No. 4.

Example 19

Production of Colored Photosensitive Composition No. 5

To 12 g of the same acrylic copolymer as that used in Example 4, 8 g of trimethylolpropane triacrylate, 2.7 g of compound No. 11 obtained in Example 2, 1.0 g of Pigment Blue 15, and 79 g of ethyl cellosolve were added, and the mixture was well stirred to obtain colored photosensitive composition No. 5.

Example 20

Production of Colored Photosensitive Composition No. 6

To 6.9 g of the same acrylic copolymer as that used in Example 4, 4.3 g of trimethylolpropane triacrylate, 2.0 g of compound No. 11 obtained in Example 2, 1.0 g of Pigment Red 254, and 87 g of ethyl cellosolve were added, and the mixture was well stirred to obtain colored photosensitive composition No. 6.

Example 21

Production of Colored Photosensitive Composition No. 7

To 12 g of the same styrene-acrylic photosensitive copolymer as that used in Example 6, 4.0 g of dipentaerythritol hexaacrylate, 1.3 g of compound No. 11 obtained in Example 2, 1.3 g of 2,2-bis(2-chlorophenyl)-4,5,4',5'-tetraphenyl-1,2'-biimidazole, 0.7 g of Pigment Red 254, 0.3 g of Pigment Yellow 138, and 83 g of ethyl cellosolve were added, and the mixture was well stirred to obtain colored photosensitive composition No. 7.

Example 22

Production of Colored Photosensitive Composition No. 8

To 12 g of the same styrene-acrylic photosensitive copolymer as that used in Example 6, 6.1 g of dipentaerythritol penta- or hexaacrylate, 2.5 g of compound No. 11 obtained in Example 2, 3.2 g of carbon black, 47 g of ethyl cellosolve, and 30 g of cyclohexanone were added, and the mixture was well stirred to obtain colored photosensitive composition No. 8.

Comparative Example 5

Production of Colored Photosensitive Composition No. 9

To 12 g of the same acrylic copolymer as that used in Example 4, 5.9 g of dipentaerythritol penta- or hexaacrylate, 2.1 g of comparative compound No. 1, 1.0 g of Pigment Blue 15, and 78 g of ethyl cellosolve were added, and the mixture was well stirred to obtain colored photosensitive composition No. 9.

Comparative Example 6

Production of Colored Photosensitive Composition No. 10

Colored photosensitive composition No. 10 was obtained under the same conditions as those in Comparative Example 5 except for using the same styrene-acrylic photosensitive copolymer as that used in Example 6 instead of the acrylic copolymer and 3.2 g of carbon black instead of 1.0 g of Pigment Blue 15.

Photosensitive compositions No. 1 to No. 15 and colored photosensitive compositions No. 1 to 10 were evaluated in the following way.

A substrate sample was coated with γ-glycidoxypropylmethylethoxysilane by spin-coating and the coating was well dried with spinning, followed by spin-coating (1300 rpm, 50 sec) with any of photosensitive compositions No. 1 to No. 15 and colored photosensitive compositions No. 1 to 10 and drying. After pre-baked at 70° C. for 20 min, 5-mass % polyvinyl alcohol solution was applied on the coating film to form an oxygen-blocking film. After dried at 70° C. for 20 min, the sample was irradiated through a given mask using a super-high pressure mercury lamp as a light source, dipped in 2.5-mass % sodium carbonate solution at 25° C. for 30 sec for development, and well washed with water. After dried, the sample was baked at 230° C. for 1 hr to fix the pattern. The resultant pattern was assessed for the following items. The results are shown in Tables 1 and 2.

<Sensitivity>

The sample for which the light value of 100 mJ/cm² was sufficient on exposure was rated at "a"; while the sample for which the light value of 100 mJ/cm² was insufficient and 200 mJ/cm² was required on exposure was rated at "b".

<Resolution>

The sample for which a well-resolved pattern was formed on development even when the line width was less than 10 µm was rated at "A", the sample for which a well-resolved pattern was formed when the line width between 10 and 30 µm was rated at "B", and the sample for which a well-resolved pattern was formed only when the line width was greater than 30 µm was rated at "C".

<Adhesiveness>

According to JIS D 0202 test method, the sample was heated at 200° C. for 30 min after exposure and development, and crosscut grooves in a chessboard pattern were formed on the coating film. Subsequently, a peeling test was performed with adhesive tape and the degree of peeling of the crosscut parts was evaluated by visual inspection. The sample in which no peeling was observed was rated at "Good" while the sample in which peeling was observed was rated at "Poor".

<Alkali Resistance>

The sample was heated at 200° C. for 30 min after exposure and development. The coating film after the heat treatment was immersed in a) 5-mass % aqueous NaOH solution for 24 hr, b) 4-mass % aqueous KOH solution at 50° C. for 10 min, or c) 1-mass % aqueous NaOH solution at 80° C. for 5 min. The appearance of the sample after immersion was evaluated by visual inspection. The sample in which neither change in appearance nor peeling of the resist was observed under any of the conditions was rated at "Good" while the sample in which lifting or peeling of the resist was observed under any of the conditions was rated at "Poor".

TABLE 1

| Photosensitive composition | Sensitivity | Resolution | Adhesion | Alkali resistance |
|---|---|---|---|---|
| No. 1 (Example 4) | a | A | Good | Good |
| No. 2 (Example 5) | a | A | Good | Good |
| No. 3 (Example 6) | a | A | Good | Good |
| No. 4 (Example 7) | a | A | Good | Good |
| No. 5 (Example 8) | a | A | Good | Good |
| No. 6 (Example 9) | a | A | Good | Good |
| No. 7 (Example 10) | a | A | Good | Good |
| No. 8 (Example 11) | a | A | Good | Good |
| No. 9 (Example 12) | a | A | Good | Good |
| No. 10 (Example 13) | a | A | Good | Good |
| No. 11 (Example 14) | a | A | Good | Good |
| No. 12 (Comparative Example 1) | b | B | Good | Poor |
| No. 13 (Comparative Example 2) | b | B | Good | Poor |
| No. 14 (Comparative Example 3) | b | C | Good | Poor |
| No. 15 (Comparative Example 4) | b | C | Good | Poor |

TABLE 2

| Colored photosensitive composition | Sensitivity | Resolution | Adhesion | Alkali resistance |
|---|---|---|---|---|
| No. 1 (Example 15) | a | A | Good | Good |
| No. 2 (Example 16) | a | A | Good | Good |
| No. 3 (Example 17) | a | A | Good | Good |
| No. 4 (Example 18) | a | A | Good | Good |
| No. 5 (Example 19) | a | A | Good | Good |
| No. 6 (Example 20) | a | A | Good | Good |
| No. 7 (Example 21) | a | A | Good | Good |
| No. 8 (Example 22) | a | A | Good | Good |
| No. 9 (Comparative Example 5) | b | B | Good | Poor |
| No. 10 (Comparative Example 6) | b | B | Good | Poor |

All of photosensitive compositions No. 1 to 11 in Examples 4 to 14 and colored photosensitive compositions No. 1 to 8 in Examples 15 to 22 were excellent in sensitivity and resolution. The resultant coating films were excellent in adhesion to the substrate and alkali resistance.

To the contrary, photosensitive compositions No. 12 to No. 15 in Comparative Examples 1 to 4 and colored photosensitive compositions No. 9 and 10 in Comparative Examples 5 and 6 required a larger light value on exposure due to their lower sensitivity, and the resolution was lowered. In addition, the resultant coating films showed poor adhesion to the substrate and poor alkali resistance.

Furthermore, the decomposition temperatures of the oxime ester compounds of the present invention are around 300° C., which are higher by 40 to 100° C. than those of the known oxime ester compounds. The oxime ester compound of the present invention was excellent in heat resistance and sufficiently stable at the temperature for heat treatment, and did not color the resultant polymerized material or contaminate the polymerized material or apparatuses.

INDUSTRIAL APPLICABILITY

The oxime ester compound of the present invention is excellent in photosensitivity and long-term stability because no precipitate was formed on the surface of photosensitive layer over time. Furthermore, using the oxime ester compound of the present invention, no decomposition product attaches to the mask and no fault in the pattern shape occurs on printing. The oxime ester compound of the present invention is, therefore, useful as a photopolymerization initiator.

The invention claimed is:

1. An oxime ester compound represented by general formula (I) below:

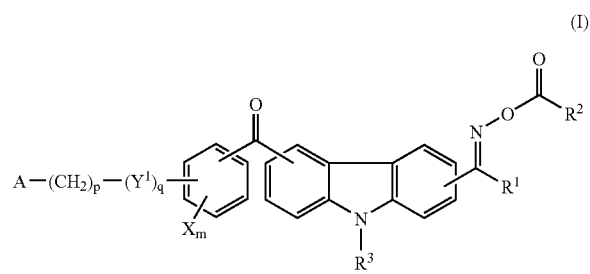

wherein X represents a halogen atom or an alkyl group; R¹, R², and R³ each independently represent R, OR, COR, SR, CONRR', or CN, wherein R and R' each independently represent an alkyl group, an aryl group, an aralkyl group, or a heterocyclic group, said groups may be substituted with one or more halogen atoms and/or one or more heterocyclic groups, said alkyl or aralkyl group has an alkylene moiety that is interrupted by one or more unsaturated bonds, one or more ether bonds, one or more thioether bonds, or one or more ester bonds, or R and R' may bond together to form a ring; $Y^1$ represents an oxygen atom, a sulfur atom, or a selenium atom; A represents a heterocyclic group; m represents an integer of 0 to 4; p represents an integer of 0 to 5; and q represents 0 or 1.

2. The oxime ester compound according to claim 1 represented by general formula (II) below:

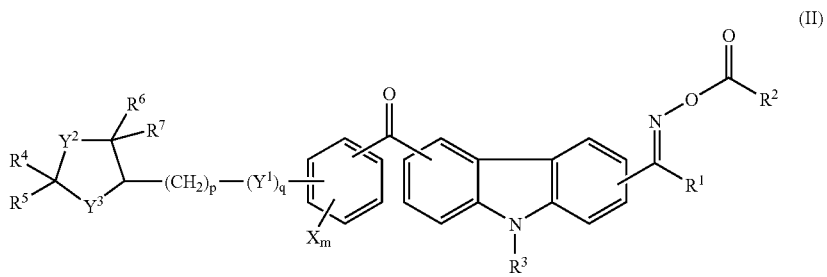

wherein $R^1$, $R^2$, $R^3$, X, $Y^1$, m, p, and q are as defined in general formula (I); $R^4$, $R^5$, $R^6$, and $R^7$ each independently represent a hydrogen atom, a halogen atom, or an alkyl group; and $Y^2$ and $Y^3$ each independently represent an oxygen atom, a sulfur atom, or a selenium atom.

3. The oxime ester compound according to claim 1 represented by general formula (III) below:

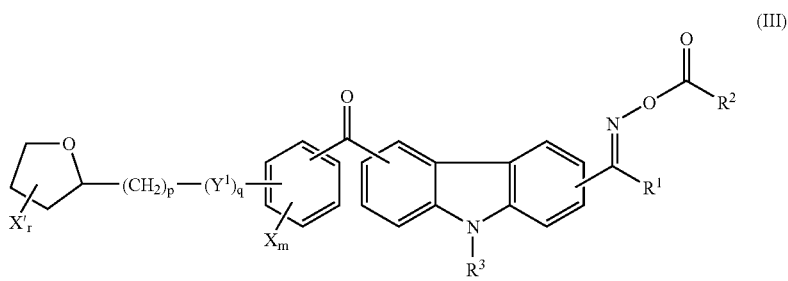

wherein $R^1$, $R^2$, $R^3$, X, $Y^1$, m, p, and q are as defined in general formula (I); X' represents a halogen atom or an alkyl group; and r represents an integer of 0 to 4.

4. The oxime ester compound according to claim 1 represented by general formula (IV) below:

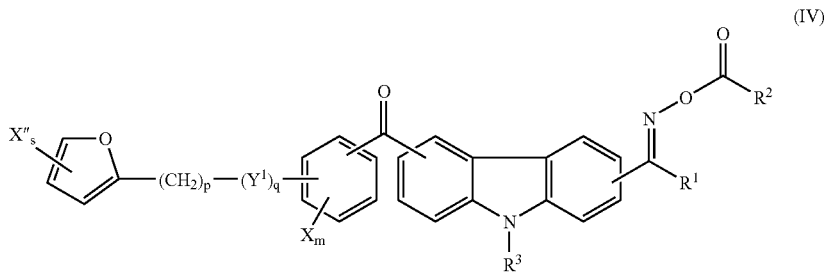

wherein $R^1$, $R^2$, $R^3$, X, $Y^1$, m, p, and q are as defined in general formula (I); X" represents a halogen atom or an alkyl group; and s represents an integer of 0 to 4.

5. The oxime ester compound according to claim 2, wherein $R^1$ is an alkyl group, $R^2$ is an alkyl group, $R^3$ is an alkyl group, $R^4$ is an alkyl group, $R^5$ is an alkyl group, $R^6$ is a hydrogen atom, $R^7$ is a hydrogen atom, X is an alkyl group, is an oxygen atom, $Y^2$ is an oxygen atom, $Y^3$ is an oxygen atom, p is 1 or 2, and q is 1 in general formula (II).

6. The oxime ester compound according to claim 3, wherein $R^1$ is an alkyl group, $R^2$ is an alkyl group, $R^3$ is an alkyl group, X is an alkyl group, $Y^1$ is an oxygen atom, p is 1 or 2, and q is 1 in general formula (III).

7. The oxime ester compound according to claim 4, wherein $R^1$ is an alkyl group, $R^2$ is an alkyl group, $R^3$ is an alkyl group, X is an alkyl group, $Y^1$ is an oxygen atom, p is 1 or 2, and q is 1 in general formula (IV).

8. A photopolymerization initiator comprising the oxime ester compound according to claim 1 as an active constituent.

9. A photosensitive composition comprising adding the photopolymerization initiator according to claim 8 to a polymerizable compound having one or more ethylenic unsaturated bonds.

10. A colored photosensitive composition comprising further adding a colorant to the photosensitive composition according to claim 9.

11. A photopolymerization initiator comprising the oxime ester compound according to claim 2 as an active constituent.

12. A photopolymerization initiator comprising the oxime ester compound according to claim 3 as an active constituent.

13. A photopolymerization initiator comprising the oxime ester compound according to claim 4 as an active constituent.

14. A photopolymerization initiator comprising the oxime ester compound according to claim 5 as an active constituent.

15. A photopolymerization initiator comprising the oxime ester compound according to claim 6 as an active constituent.

16. A photopolymerization initiator comprising the oxime ester compound according to claim 7 as an active constituent.

* * * * *